United States Patent
Vaid et al.

(10) Patent No.: US 10,294,276 B2
(45) Date of Patent: May 21, 2019

(54) PROCESS FOR ISOLATION OF ROMIDEPSIN FROM FERMENTATION BROTH AND PREPARATION OF CRYSTALS OF ROMIDEPSIN

(71) Applicant: Concord Biotech Limited, Gujarat (IN)

(72) Inventors: Ankur S. Vaid, Gurjarat (IN); Anand M. Dhiman, Gurjarat (IN); Traunkant P. Sharma, Gurjarat (IN)

(73) Assignee: Concord Biotech Limited, Gujarat (IN)

( * ) Notice: Subject to any disclaimer, the term of this patent is extended or adjusted under 35 U.S.C. 154(b) by 0 days.

(21) Appl. No.: 15/123,295

(22) PCT Filed: Mar. 2, 2015

(86) PCT No.: PCT/IN2015/000113
§ 371 (c)(1),
(2) Date: Sep. 2, 2016

(87) PCT Pub. No.: WO2015/136548
PCT Pub. Date: Sep. 17, 2015

(65) Prior Publication Data
US 2017/0073374 A1    Mar. 16, 2017

(30) Foreign Application Priority Data
Mar. 4, 2014   (IN) .......................... 740/MUM/2014

(51) Int. Cl.
*C07K 11/02*    (2006.01)
*C07K 5/103*    (2006.01)

(52) U.S. Cl.
CPC .............. *C07K 11/02* (2013.01); *C07K 5/101* (2013.01)

(58) Field of Classification Search
None
See application file for complete search history.

(56) References Cited

U.S. PATENT DOCUMENTS 4,977,138 A * 12/1990 Okuhara ................ C07K 5/101
                                                          514/19.3
7,396,665 B2 * 7/2008 Ueda ....................... C12P 21/02
                                                          435/106

* cited by examiner

*Primary Examiner* — Maury A Audet
(74) *Attorney, Agent, or Firm* — Blank Rome LLP

(57) ABSTRACT

The present invention describes a process for isolation of romidepsin from fermentation broth and preparation of crystals of romidepsin. The process of the invention includes fewer purification steps and provides romidepsin having purity of greater than 99.5% area by HPLC. The process of the invention involves simple purification steps and hence, does not require multiple chromatographic purification steps to achieve desired quality of romidepsin. The process is advantageous over reported processes in terms of 99.5% pure yield, fast process, less expensive and less cumbersome as multiple chromatographic purification is not necessary to achieve desired quality. The process for the preparation of crystals of romidepsin provides advantages like simple steps and involves use of single solvent. The process is advantageous in terms of time, cost, and simplicity.

9 Claims, 4 Drawing Sheets

PROCESS FOR ISOLATION OF ROMIDEPSIN FROM FERMENTATION BROTH AND PREPARATION OF CRYSTALS OF ROMIDEPSIN

RELATED APPLICATIONS

This application is a national stage application of International Application No. PCT/IN2015/000113, filed Mar. 2, 2015, which is related to and claims priority to Indian Patent Application No. 740/MUM/2014, filed Mar. 4, 2014, the entire disclosures of which are hereby incorporated by reference.

FIELD OF THE INVENTION

The present invention provides a process for the isolation of romidepsin and a process for the preparation of romidepsin crystalline form.

BACKGROUND OF THE INVENTION

Romidepsin, also known as FK228 and FR901228, is a potent histone deacetylase inhibitor. The chemical structure of romidepsin is depicted below as Formula I.

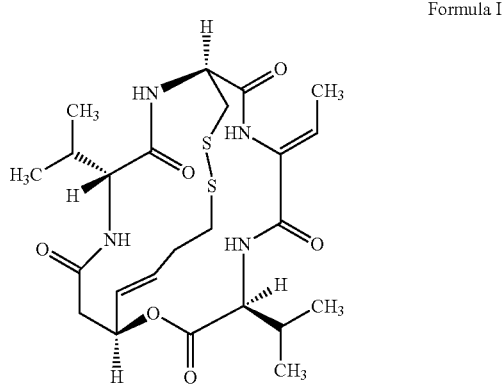 [SMILES: C/C=C1\NC(=O)[C@H]2CSSCC/C=C/[C@H](CC(=O)N[C@H](C(C)C)C(=O)N2)OC(=O)[C@H](C(C)C)NC1=O]

Formula I

U.S. Pat. No. 4,977,138 describes preparation of romidepsin by culturing microorganism *Chromobacterium violaceum* WB968. Romidepsin is isolated from fermentation broth by extraction and column chromatography.

U.S. Pat. No. 7,396,665 provides an alternative process for the preparation of romidepsin which requires carrying out four column chromatographic purifications steps.

US2009/0186382 states that above published processes for the isolation of romidepsin does not produce pure romidepsin consistently. US'382 application then goes on to describe an alternative process for the preparation of pure romidepsin to avoid drawbacks of above published processes. US'382 process is carried out at specific pH range and involves use of four chromatographic purifications and two crystallization steps.

A process disclosed in U.S. Pat. No. 4,977,138 for the preparation of romidepsin crystal requires use of three solvents and provides crystals having higher residual solvent content. An improved process described in U.S. Pat. No. 7,611,724 involves use of two solvents which must be used in the specific concentration. Hence, there is a need to provide a simpler process which has a small number of purification steps and requires less time for the isolation of pure romidepsin.

OBJECT OF THE INVENTION

The main object of the present invention is to provide an improved process for the isolation of romidepsin.

Another object of the present invention is to provide a process for the preparation of crystals of romidepsin.

SUMMARY OF THE INVENTION

The present invention provides an improved process for the isolation of romidepsin from the fermentation broth. The fermentation broth is produced by culturing a microorganism, *Chromobacterium violaceum*, by the method known in the art to produce fermentation broth.

An embodiment of the invention provides a process for the whole broth extraction of romidepsin. The whole broth extraction does not require separation of any ingredient of the broth before the extraction of romidepsin. Hence, step of filtration or separation of any broth ingredient is not required which makes isolation process simpler.

The present invention provides single solvent process for the preparation of crystals of romidepsin by three steps:
a) dissolving romidepsin in a solvent to obtain a solution
b) initiating precipitation of romidepsin
c) recovering crystals of romidepsin

DETAILED DESCRIPTION OF THE INVENTION

Figure 1:
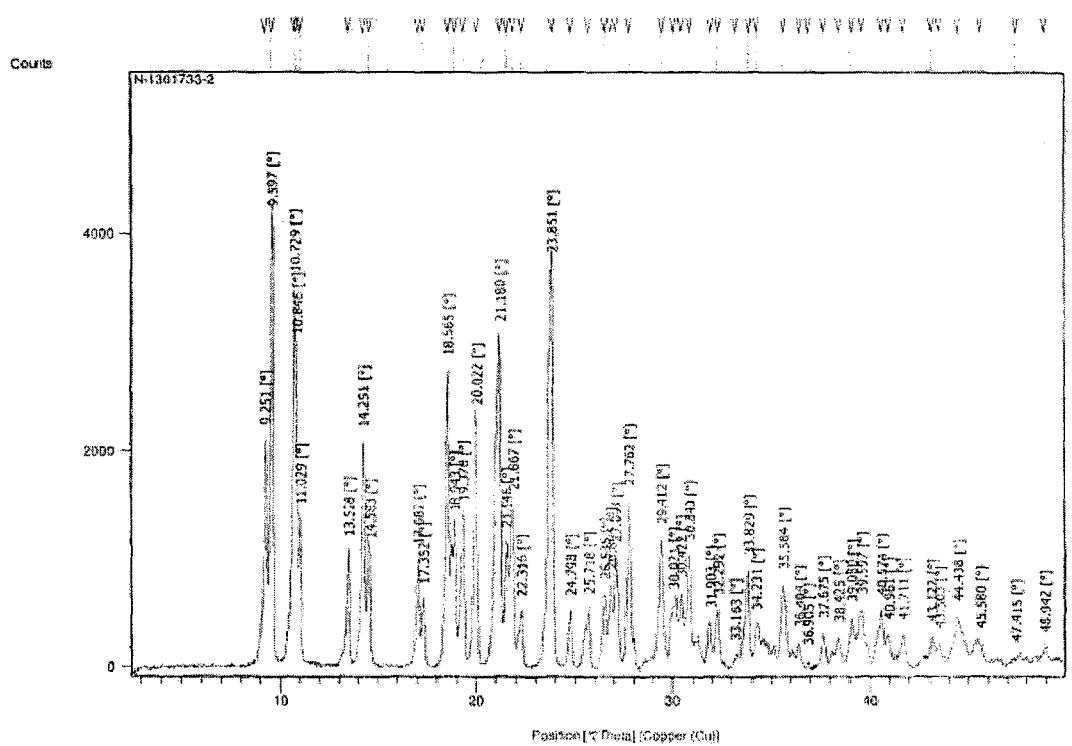
FIG. 1 refers to x-ray diffractogram of crystals of romidepsin

Before explaining the present invention in detail, it is to be understood that the invention is not limited in its steps and concentration, mentioned hereafter to obtain romidepsin from fermentation broth by said components. The nature of the invention along with various components is described in the following pages. It is to be understood that the phraseology and terminology employed herein is for the purpose of description and not of limitation.

The term "romidepsin", "FK228" and "FR901228" are used interchangeably and refer to the compound of Formula I.

The term "isolation of romidepsin" refers to a process of separating romidepsin in a powder form from the fermentation broth. In general, isolation includes one or more steps selected from extraction, chromatography and crystallization.

The term "fermentation broth" refers to the broth obtained by culturing a microorganism capable of producing romidepsin, for example *Chromobacterium violaceum*. The fermentation broth can be prepared by the process described in prior art, for example U.S. Pat. No. 4,977,138.

The term "crystals of romidepsin" refers to the crystalline form of romidepsin which is similar to crystals obtained in U.S. Pat. No. 4,977,138 when compared by XRD, DSC and melting point.

The fermentation broth is extracted using an organic solvent which is capable of separating romidepsin from the broth. The organic solvent for the extraction step includes, but not limited to, isobutyl acetate, isopropyl acetate, ethyl acetate and toluene. Preferably, the fermentation broth is extracted using toluene. Extraction is carried out using from about one to about two volume of an organic solvent at a room temperature. Extraction step may be repeated if required. After the completion of extraction, an organic solvent is evaporated under reduced pressure. Evaporation is carried out at a temperature from about 25° to 40° C.

An organic solvent is added to the obtained residue. Preferably, the organic solvent is a ketone or nitrile solvent for example acetone, methyl isobutyl ketone and acetonitrile. Most preferably, methyl isobutyl ketone is added to the residue. The solvent is added in an amount of about 50 to 100 volumes with respect to active romidepsin content in the residue. The content of active romidepsin in the residue is determined by HPLC method. Romidepsin gets dissolved in the organic solvent and non-dissolved impurities are removed by filtration. The solvent is evaporated from the filtrate under reduced pressure at a temperature from about 25° to 40° C. to give a residue.

Preferably, an ester solvent is added to the obtained residue to get the clear solution. Most preferably, an ester solvent is ethyl acetate. The obtained solution is subjected to silica gel column chromatography. Chromatography is performed on silica gel of 60-120 mesh or 230-400 mesh using a mobile phase prepared from acetone-heptane, ethyl acetate-cyclohexane or dichloromethane-hexane. Fractions containing romidepsin are pooled and evaporated under reduced pressure at a temperature from about 25° to 40° C. to give a residue.

An organic solvent is added to the residue in an amount of about 15 to about 20 volumes. Preferably, the organic solvent is a ketone or a nitrile solvent for example methyl isobutyl ketone and acetonitrile. Most preferably, the organic solvent is methyl isobutyl ketone. Solid romidepsin, thus obtained is filtered and purified by crystallization from an organic solvent selected from ketone or alcohol. Preferably, crystallization solvent is acetone, 2-butanone, methanol, isopropyl alcohol, butyl alcohol or a mixture thereof.

An embodiment of the invention provides a process for the isolation of romidepsin which comprises
a) extracting the fermentation broth with an organic solvent and evaporating the solvent to obtain a residue;
b) treating the residue with an organic solvent and evaporating the solvent to obtain a residue;
c) subjecting the residue to silica gel column chromatography;
d) treating the product of step c) with an organic solvent;
e) crystallizing the product obtained in step d).

A preferred embodiment of the invention provides an improved process for the isolation of romidepsin from the fermentation broth which comprises
a) extracting the fermentation broth with an organic solvent;
b) evaporating the organic solvent to give oily residue;
c) adding an organic solvent to the residue;
d) evaporating the organic solvent to give oily residue;
e) adding an ester solvent to the residue;
f) subjecting the ester solution to the silica gel column;
g) evaporating the solvent from the romidepsin containing fractions;
h) adding an organic solvent to the residue;
i) filtering the solid thus obtained;
j) crystallizing the solid from an organic solvent to give pure romidepsin.

An embodiment of the invention provides an improved process for the isolation of romidepsin from the fermentation broth which provides romidepsin having purity of greater than 99.5% by area in HPLC.

The improved process of the invention involves simple purification steps and hence, does not require multiple chromatographic purification steps to achieve desired quality of romidepsin. The process is advantageous over reported processes in terms of time, cost and simplicity.

The present invention also provides a process for the preparation of crystals of romidepsin.

An embodiment of the invention provides a single solvent process for the preparation of crystals of romidepsin which comprises
a) dissolving romidepsin in a solvent to obtain a solution
b) initiating precipitation of romidepsin
c) recovering crystals of romidepsin Step a) involves dissolution of romidepsin in a solvent by mixing romidepsin and a solvent. The resultant mixture may be heated and filtered to obtain a clear solution. Preferably, the solvent is a chlorinated hydrocarbon or an ester, for example dichloromethane, chloroform, ethyl acetate, isopropyl acetate, isobutyl acetate and like that.

Precipitation of romidepsin in step b) is initiated by either allowing the solution to stand at a temperature lower than 25° C. or evaporating the solution to the reduced volume. After initiation of precipitation, the solution is stirred for a period of about 10 minutes to about 1 hour.

Crystals of romidepsin is recovered in step c) by conventional method like filtration.

EXAMPLES

The following examples are presented to illustrate the invention and do not limit the scope of the invention. It should be understood that although specific embodiments are outlined in the examples, modifications can be made which are included within the scope of the invention.

Isolation of Romidepsin

Harvested broth (1000 lit) received from fermentation was charged to Reactor. Toluene (1000 lit) was added to the broth and agitated for two hour. The mixture was filtered through hyflo bed and layers were separated. Toluene was distilled under reduced pressure at 35° C. up to 500 L. The precipitated solid was filtered out through hyflo bed. Hyflo bed was washed with toluene. Toluene was distilled under reduced pressure at 35° C. to give oily residue. MIBK (Methyl isobutyl keton) was added to the oily residue and stirred for half hour. The solution was filtered through hyflo bed. MIBK (Methyl isobutyl keton) was distilled under reduced pressure at 30° C. to give oily residue. Ethyl acetate was added to the oily residue to get a solution.

Figure 4:
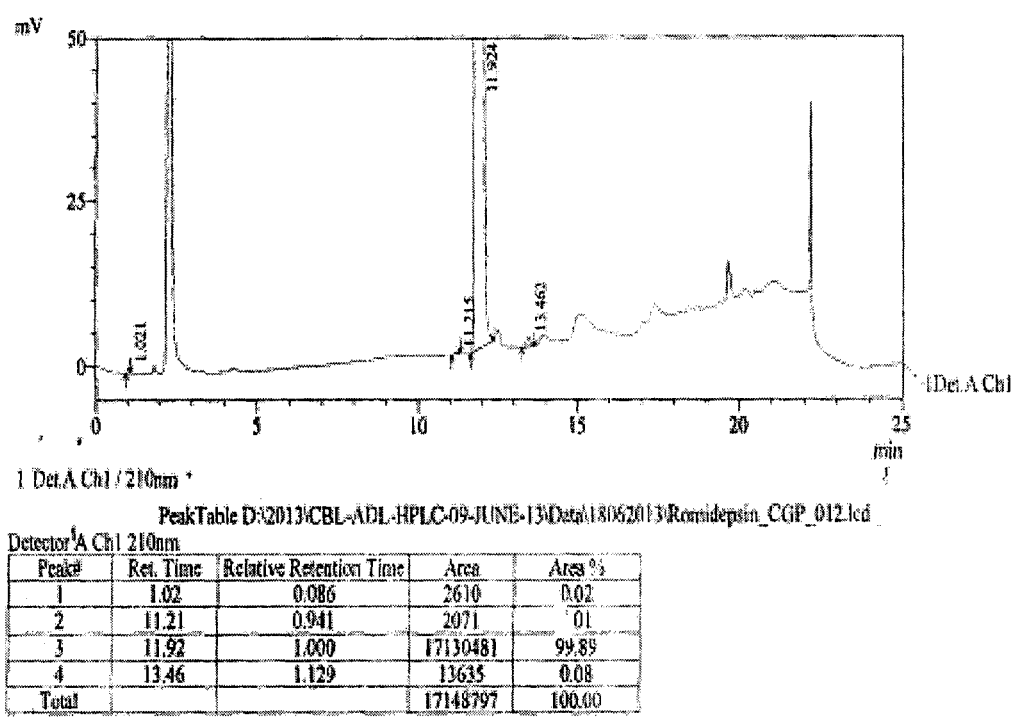
FIG. 4 refers to HPLC chromatogram of romidepsin

Ethyl acetate solution was loaded to packed column [Silica gel (230-400 mesh): 30-35 lit]. The column was eluted using a mobile phase prepared from dichloromethane and hexane. Fractions containing compound were pooled and distilled under reduced pressure at 35° C. to give oily residue. MIBK (Methyl isobutyl keton) was added to the residue and stirred for half hour. The solid obtained was filtered and suck dried for one hour to obtain a crude romidepsin. Crude romidepsin was dissolved in acetone at 50° C. and stirred overnight at room temperature. The solid obtained was filtered and suck dried for 1 hour to obtain pure romidepsin. FIG. 4 shows HPLC purity of isolated romidepsin which was found to be 99.89% by area.

Preparation of Romidepsin Crystals

Figure 2:
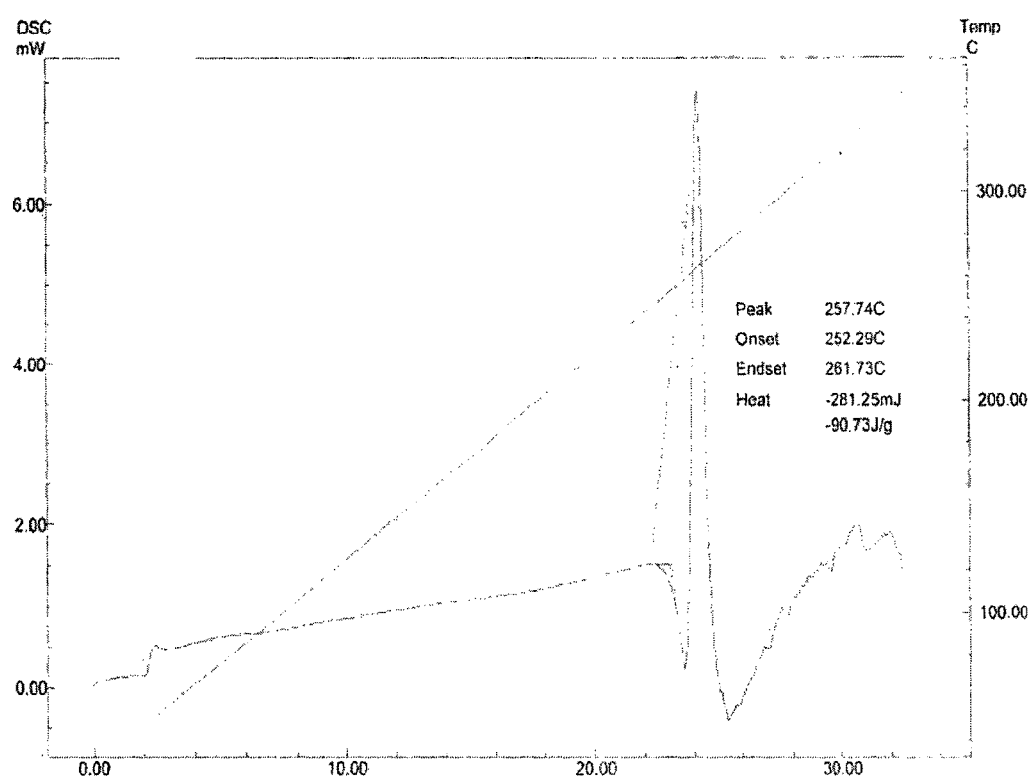
FIG. 2 refers to DSC thermogram of crystals of romidepsin
Figure 3:
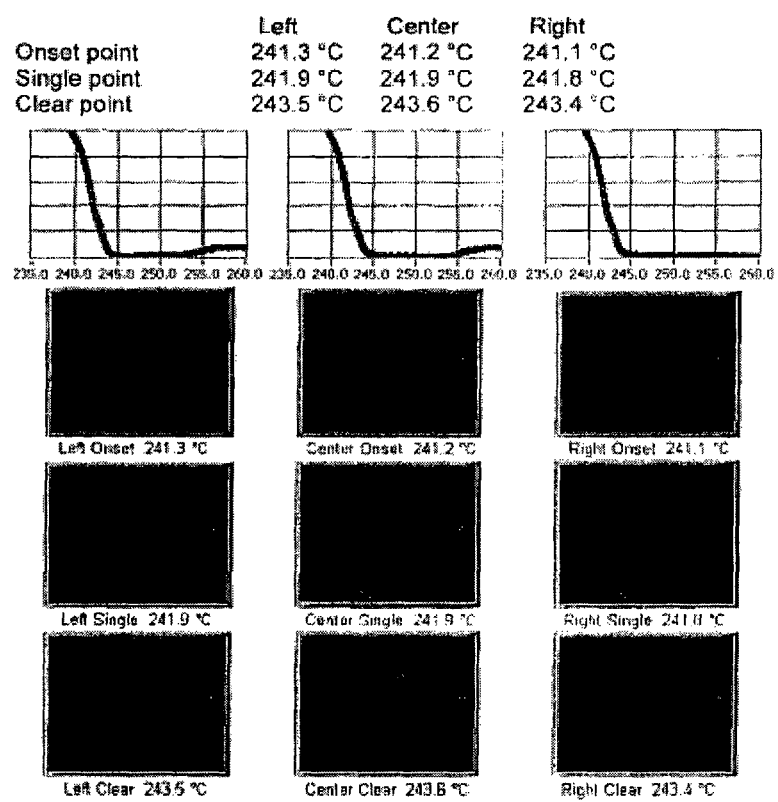
FIG. 3 refers to MP data of crystals of romidepsin

Romidepsin was dissolved in dichloromethane at 50° C. The solution was filtered through hyflo bed. Hyflo bed was washed with dichloromethane. The solution was reduced to 75% under vacuum. Solid obtained was filtered and dried under reduced pressure at 50° C. to obtain crystals of romidepsin. The result of this process is shown in FIG. 1-3 as they respectively shows X-ray diffraction, DCS thermogram and Melting point study of romidepsin drug crystals.

We claim:

1. A process for the isolation of romidepsin from a fermentation broth which comprises,
   a) extracting the romidepsin from the fermentation broth with an organic solvent and evaporating the solvent to obtain a residue, wherein the organic solvent is selected from the group consisting of isobutyl acetate, isopropyl acetate, ethyl acetate, and toluene;
   b) treating the residue obtained in step a) with an amount of methyl isobutyl ketone or acetonitrile from about 50 to 100 volumes with respect to the content of romidepsin in the residue determined by HPLC to obtain a residue and removing non-dissolved impurities by filtration followed by evaporating the filtrate;
   c) subjecting the residue obtained in step b) to silica gel column chromatography using a silica gel of 60-120 mesh or 230-400 mesh to obtain a product;
   d) treating the product of step c) with an organic solvent selected from the group consisting of methyl isobutyl ketone or acetonitrile to produce a second product; and
   e) crystallizing the second product obtained in step d) to obtain romidepsin, wherein romidepsin is characterized as having a purity of greater than 99.5%.

2. The process according to claim 1, wherein step c) is performed using a mobile phase selected from one of acetone-heptane, ethyl acetate-cyclohexane, and dichloromethane-hexane.

3. The process according to claim 1, further comprising step f), which comprises,
   a) dissolving an amount of romidepsin in a solvent to obtain a solution;
   b) initiating precipitation of the romidepsin from the solution; and
   c) recovering the crystals of romidepsin.

4. The process according to claim 3, wherein the amount of romidepsin is dissolved in one of a chlorinated hydrocarbon or an ester solvent in step a).

5. The process according to claim 3, wherein the precipitation of romidepsin crystals in step b) is initiated by allowing the solution to stand at a temperature lower than 25° C. or evaporating the solution to a reduced volume.

6. The process according to claim 3, wherein the precipitation of romidepsin crystals in step b) is initiated by evaporating the solution to a reduced volume.

7. The process according to claim 3, wherein the crystal of romidepsin is characterized by an X-ray diffractogram substantially as depicted in FIG. 1.

8. The process according to claim 3, wherein the crystal of romidepsin is characterized by a DSC thermogram substantially as depicted in FIG. 2.

9. The process according to claim 1, wherein step e) is carried out using one of a ketone or an alcohol.

* * * * *